United States Patent
Kim et al.

(10) Patent No.: US 9,588,048 B2
(45) Date of Patent: Mar. 7, 2017

(54) SURFACE ENHANCED RAMAN SPECTROSCOPY SENSOR, SYSTEM AND METHOD OF SENSING

(75) Inventors: Ansoon Kim, Mountain View, CA (US); Zhiyong Li, Foster City, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 246 days.

(21) Appl. No.: 14/118,801

(22) PCT Filed: May 20, 2011

(86) PCT No.: PCT/US2011/037464
§ 371 (c)(1),
(2), (4) Date: Nov. 19, 2013

(87) PCT Pub. No.: WO2012/161683
PCT Pub. Date: Nov. 29, 2012

(65) Prior Publication Data
US 2014/0125976 A1    May 8, 2014

(51) Int. Cl.
*G01N 21/65*    (2006.01)
*G01J 3/44*    (2006.01)
*B82Y 15/00*    (2011.01)

(52) U.S. Cl.
CPC ............ *G01N 21/658* (2013.01); *G01J 3/44* (2013.01); *B82Y 15/00* (2013.01)

(58) Field of Classification Search
CPC .......... G01N 21/65; G01N 21/658; G01J 3/44
See application file for complete search history.

(56) References Cited

U.S. PATENT DOCUMENTS 6,149,868 A * 11/2000 Natan et al. ............... 422/82.05
7,342,656 B2    3/2008 Islam et al.
(Continued)

FOREIGN PATENT DOCUMENTS

CN    101281133 A    10/2008
CN    101680900 A    3/2010
(Continued)

OTHER PUBLICATIONS

Min Hu, Fung Suong Ou, Wei Wu, Ivan Naumov, Xuema Li, Alexander M. Bratkovsky, R. Stanley Williams, and Zhiyong Li, "Gold Nanofingers for Molecule Trapping and Detection," Published on Web Aug. 26, 2010, J. Am. Chem. Soc. 2010, 132, p. 12820-12822.*

(Continued)

*Primary Examiner* — Kara E Geisel
*Assistant Examiner* — Violeta A Prieto
(74) *Attorney, Agent, or Firm* — North Shore Associates (57) ABSTRACT

A surface enhanced Raman spectroscopy (SERS) sensor, system and method employ nanorods and independent nanoparticles that interact. The sensor includes at least two spaced apart nanorods attached at first ends to a substrate and an independent nanoparticle. Second ends of the nanorods are movable into close proximity to one another and include a Raman active surface. The nanoparticle has a functionalized surface that includes a Raman signal generator. An interaction between the nanoparticle and the nanorod second ends in close proximity is detectable. The system includes the SERS sensor, an illumination source and a Raman signal detector. The method includes illuminating the interaction of the nanoparticle and the nanorods with an analyte, and detecting an effect on a Raman signal caused by the analyte.

11 Claims, 6 Drawing Sheets

(56) References Cited

U.S. PATENT DOCUMENTS

| | | | |
|---|---|---|---|
| 7,880,876 B2 | 2/2011 | Zhao et al. | |
| 8,477,303 B2 | 7/2013 | Bratkovski et al. | |
| 8,767,202 B2 * | 7/2014 | Schmidt | G01N 21/658 356/301 |
| 2002/0142480 A1 | 10/2002 | Natan | |
| 2003/0059820 A1 * | 3/2003 | Vo-Dinh | 435/6 |
| 2005/0158877 A1 * | 7/2005 | Wang et al. | 436/524 |
| 2005/0196870 A1 | 9/2005 | Sun | |
| 2006/0146323 A1 | 7/2006 | Bratkovski et al. | |
| 2006/0252065 A1 | 11/2006 | Zhao et al. | |
| 2007/0086001 A1 * | 4/2007 | Islam et al. | 356/301 |
| 2008/0241569 A1 | 10/2008 | Qin et al. | |
| 2009/0325318 A1 | 12/2009 | Carron | |
| 2010/0173347 A1 | 7/2010 | Brook et al. | |
| 2010/0183875 A1 | 7/2010 | Mao et al. | |
| 2010/0231242 A1 | 9/2010 | Gabriel et al. | |
| 2011/0116089 A1 | 5/2011 | Schmidt et al. | |
| 2011/0228266 A1 | 9/2011 | Kuo et al. | |
| 2012/0188539 A1 | 7/2012 | Stuke et al. | |
| 2013/0027698 A1 | 1/2013 | Li et al. | |
| 2013/0040862 A1 | 2/2013 | Li et al. | |
| 2013/0195721 A1 | 8/2013 | Li et al. | |
| 2013/0217143 A1 | 8/2013 | Li et al. | |
| 2015/0362486 A1 | 12/2015 | Li et al. | |

FOREIGN PATENT DOCUMENTS

| | | |
|---|---|---|
| CN | 101978254 A | 2/2011 |
| CN | 102282094 | 12/2011 |
| CN | 102834709 | 12/2012 |
| CN | 102947681 | 2/2013 |
| EP | 2320216 A2 | 5/2011 |
| EP | 2365935 | 9/2011 |
| EP | 2561322 | 2/2013 |
| EP | 2561337 | 2/2013 |
| JP | 2009-544967 | 12/2009 |
| JP | 2010-25753 A | 2/2010 |
| JP | 2011-081001 | 4/2011 |
| JP | 2012508881 | 4/2012 |
| JP | 2013-525785 | 6/2013 |
| JP | 2013-527921 | 7/2013 |
| JP | 5497963 | 5/2014 |
| JP | 5519075 | 6/2014 |
| KR | 102011009783 | 8/2011 |
| TW | I418785 | 10/2007 |
| TW | 201111771 A | 4/2011 |
| WO | WO-2008116093 | 9/2008 |
| WO | WO-2010056258 | 5/2010 |
| WO | WO-2011133143 | 10/2011 |
| WO | WO-2011133144 | 10/2011 |
| WO | WO-2012054024 | 4/2012 |
| WO | WO-2012054027 | 4/2012 |

OTHER PUBLICATIONS

Ansoon Kim et al, Study of Molecular Trapping Inside Gold Nanofinger Arrays on Surface-Enhanced Raman Substrates; Journal of the American Chemical Society; pp. 8234-8239.

Yuling Wang et al; SERS aptasensor from nanorod-nanoparticle junction for protein detection; The Royal Society of Chemistry 2010; pp. 613-615.

PCT International Search Report, Jan. 11, 2012, Patent Application No. PCT/US2011/037464.

Shi, Chao et al., CLEO/QELS 2008, May 4, 2008, paper CMJJ1.

White, Daniel J. et al., ACOFT/AOS 2006, Jul. 10, 2006, pp. 63-65.

Qiu, T., et al. "Surface-enhanced Raman characteristics of Ag cap aggregates on silicon nanowire arrays." 14 Dec. 2006, Nanotechnology vol. 17, No. 23, pp. 5769-5772.

* cited by examiner

SURFACE ENHANCED RAMAN SPECTROSCOPY SENSOR, SYSTEM AND METHOD OF SENSING

STATEMENT REGARDING FEDERALLY SPONSORED RESEARCH OR DEVELOPMENT

This invention has been made with government support awarded by Defense Advanced Research Projects Agency. The government has certain rights in the invention.

CROSS-REFERENCE TO RELATED APPLICATIONS

N/A

BACKGROUND

Detection and identification (or at least classification) of unknown substances have long been of great interest and have taken on even greater significance in recent years. Among methodologies that hold particular promise for precision detection and identification are various forms of spectroscopy, especially those that employ Raman scattering. Spectroscopy may be used to analyze, characterize and identify a substance or material using one or both of an absorption spectrum and an emission spectrum that results when the material is illuminated by a form of electromagnetic radiation (e.g., visible light). The absorption and emission spectra produced by illuminating the material determine a spectral 'fingerprint' of the material. In general, the spectral fingerprint is characteristic of the particular material facilitating identification of the material. Among the most powerful of optical emission spectroscopy techniques are those based on Raman scattering.

Raman scattering optical spectroscopy or simply Raman spectroscopy employs an emission spectrum or spectral components thereof produced by inelastic scattering of photons by an internal structure of the material being illuminated. These spectral components contained in a response signal (e.g., a Raman scattering signal) produced by the inelastic scattering may facilitate determination of the material characteristics of an analyte species including, but not limited to, identification of the analyte. Surface enhanced Raman scattering (SERS) optical spectroscopy is a form of Raman spectroscopy that employs a Raman-active surface. SERS may significantly enhance a signal level or intensity of the Raman scattering signal produced by a particular analyte species.

BRIEF DESCRIPTION OF THE DRAWINGS

Various features of examples of the principles described herein may be more readily understood with reference to the following detailed description taken in conjunction with the accompanying drawings, where like reference numerals designate like structural elements, and in which.

Certain examples have other features that are one of in addition to and in lieu of the features illustrated in the above-referenced figures. These and other features are detailed below with reference to the preceding drawings.

DETAILED DESCRIPTION

SERS may be useful in a wide variety of detection and identification analysis applications. However, there may be instances where the analyte species to be detected, for example a biological or chemical species, may be difficult to detect using SERS. For example, the amount of the analyte species may be too small or too dilute to detect, or the molecules of the analyte species may be too bulky or cumbersome to capture for detection or to create Raman 'hot-spots' with a few nanometer-sized gaps. Examples in accordance with the principles described herein provide for detection of bulky molecules and minute quantities of a variety of analyte species.

In some examples, a SERS sensor is provided that comprises a sensing substrate that includes at least two nanorods spaced apart on the substrate. The nanorods are anchored at first ends to the substrate and are movable into close proximity to one another at second ends of the nanorods. The nanorods include a Raman active surface. The SERS sensor further comprises a nanoparticle facilitates an interaction between the nanoparticle and the nanorods that is detectable, for example an interaction that may involve or is affected by an analyte.

In some examples, a SERS sensor system is provided that comprises a SERS sensor that includes both the nanorod sensing substrate and the functionalized nanoparticles, and further includes an illumination source directed at the nanorod second ends when in close proximity, and a Raman signal detector arranged to detect a Raman signal from a vicinity of the nanorod second ends in close proximity. In some examples, a method of SERS sensing is provided that comprises exposing the SERS sensor to an analyte, illuminating the nanorod second ends in close proximity to generate a Raman signal, and detecting an effect on the Raman signal caused by the analyte. In some examples, the SERS sensor system and the method may provide multiplexing of a variety of analytes with the SERS sensor.

As used herein, the article 'a' is intended to have its ordinary meaning in the patent arts, namely 'one or more'. For example, 'a nanoparticle' means one or more nanoparticles and as such, 'the nanoparticle' explicitly means 'the nanoparticle(s)' herein. Also, any reference herein to 'top', 'bottom', 'upper', 'lower', 'up', 'down', 'front', back', 'first', 'second', 'left' or 'right' is not intended to be a limitation herein. Herein, the term 'about' when applied to a value generally means plus or minus 10%, or within normal tolerances of a measurement technique used, unless otherwise expressly specified. Any ranges of values provided herein include values and ranges within or between the provided ranges. Moreover, examples herein are intended to be illustrative only and are presented for discussion purposes and not by way of limitation.

A 'nanorod' herein is defined as an elongated, nanoscale structure having a length (or height) that exceeds by more than several times a nanoscale cross sectional dimension (e.g., width) taken in a plane perpendicular to the length (e.g., length greater than about 2 times the width). In general, the length of the nanorod is much greater than the nanorod width or cross sectional dimension. In some examples, the length exceeds the cross sectional dimension (or width) by more than a factor of 4 to a factor of 10. For example, the width may be about 130 nanometers (nm) and the height may be about 500 nm. In another example, the width at a base of the nanorod may range between about 20 nm and about 200 nm and the length may be more than about a 0.5 micrometer (μm). In some examples, the nanorod is generally columnar in shape with a curvilinear or faceted perimeter in cross section. In another example, the nanorod may be conical with a base having a width ranging from between about 100 nm and about 500 nm and a length or height that may range between about one-half and several micrometers. In some examples, the nanorod is flexible; in other examples, the nanorod is rigid or semi-rigid provided that free ends of adjacent nanorods can move into close proximity to one another, as described further below.

A 'nanoparticle' herein is defined as a nanoscale structure having substantially similar dimensions of length, width and depth. For example, the shape of a nanoparticle may be a circle, an ellipsoid, or a faceted circle or ellipsoid, or a cube, a pentagon or a hexagon, and so on. The size of the nanoparticle may range from about 5 nm to about 200 nm, for example, in diameter. In some examples, the nanoparticle diameter may be within a range of about 50 nm to about 100 nm, or about 25 nm to about 100 nm, or about 100 nm to about 200 nm, or about 10 nm to about 150 nm, or about 20 nm to about 200 nm. Further as defined herein, the 'nanoparticle' is distinguished from a 'nanoparticle catalyst' or 'catalyst nanoparticle' and a layer or coating of nanoparticles mentioned below. In particular, the 'nanoparticle', as defined herein, is free or independent of a nanorod, whereas each of the nanoparticle catalyst and the nanoparticle layer or coating, as described herein, is considered to be an integral portion of the nanorod that has a different function compared to the 'nanoparticle'.

Figure 1:
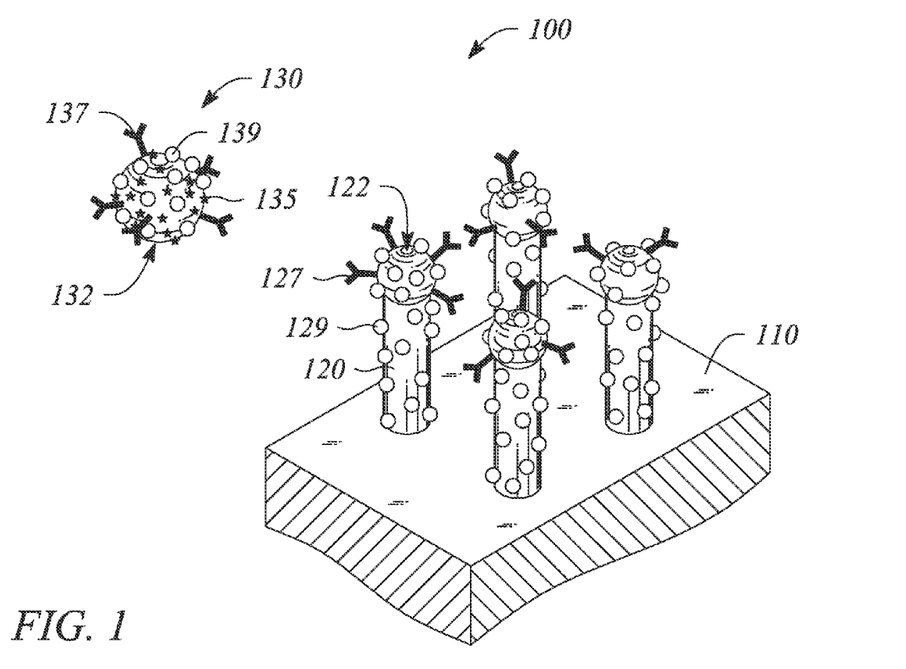
FIG. 1 illustrates a schematic perspective view of a surface enhanced Raman spectroscopy (SERS) sensor according to an example in accordance with the principles described herein.

FIG. 1 illustrates a schematic perspective view of a SERS sensor 100 according to an example of the principles described herein. The SERS sensor 100 comprises a nanoparticle 130 having a functionalized surface 132 and a sensing substrate 110 having a surface populated with at least two adjacent nanorods 120 spaced apart on the substrate surface. The nanoparticle 130 is independent of and is provided to interact with the nanorods 120. In some examples, there may be multiples of two, or three, or four, or five, or six, and so on, spaced apart nanorods 120 on the surface of the substrate 110. Moreover, the spaced apart nanorods 120 may be grouped into multiples sets of at least two adjacent nanorods on the substrate surface. FIG. 1 illustrates four of such adjacent nanorods 120 by way of example and for simplicity of illustration.

The nanorods 120 are fabricated on the substrate surface using any of a variety of techniques including, but not limited to, a three-dimensional imprinting method, embossing, a chemical vapor deposition (CVD) growth process, etching and a roll-to-roll process. In some examples, nanowire growth may employ one of a vapor-solid (V-S) growth process and a solution growth process. In other examples, growth may be realized through directed or stimulated self-organization techniques such as, but not limited to, focused ion beam (FIB) deposition and laser-induced self assembly. In another example, the nanorods may be produced by using an etching process such as, but not limited to, reactive ion etching, to remove surrounding material leaving behind the nanorods.

Each nanorod 120 is anchored or attached to the substrate 110 at a first end and has a second, opposite end 122 that is free or unattached. The second ends 122 of the nanorods 120 have a tip that may be either a rounded (e.g., domed) shape, as illustrated in the figures herein, by way of example, a substantially flattened or a substantially pointed tip (both not illustrated). For example, the nanorod 120 may have a tip that results naturally from a process (e.g., VLS growth) used to realize the nanorod 120. In other examples, the tip may be further processed to impart a particular shape to the second end 122 of the nanorod 120. For example, the tips may be flattened using chemical-mechanical polishing, for example. By 'pointed' it is meant that the tip tapers from a cross sectional size of the nanorod 120 to a terminus at the second end 122. The terminus generally has a relatively acute angle of inflection between surfaces of the tip leading up to the terminus.

In some examples, the nanorods 120 may comprise a catalyst nanoparticle at the tip of the second end 122, for example as a result of the process used to form the nanorods 120 (e.g., catalyzed VLS growth). In these examples, the catalyst nanoparticle tip at the second end 122 is integral to the nanorod 120. By 'integral' it is meant that the nanorod 120 is formed with the nanoparticle catalyst at its tip (i.e., the nanoparticle catalyst is considered a part of the nanorod herein). Examples of nanoparticle catalyst materials include, but are not limited to, gold-silicon alloy and titanium silicide ($TiSi_2$). In some examples, the nanoparticle catalyst may be a Raman-active material that further imparts a nanoscale surface roughness to enhance a Raman active surface of the nanorods 120.

In some examples, the nanorods 120 are made of a material having sufficient flexibility to bend along their length. In some examples, the nanorods 120 may comprise an inorganic material having sufficient flexibility to bend. In other examples, the nanorods 120 comprise a polymeric material having sufficient flexibility to bend. The nanorod material is sufficiently flexible to bend so that second ends 122 of adjacent spaced apart nanorods 120 can move into close proximity to one another. By 'close proximity' it is meant that the nanorod second ends 122 move to within 0 to about 10 nm of each other, or 0 to about 15 nm of each other, or to within a distance of each other to sufficiently concentrate a Raman signal when illuminated by an illumination source. For example, the nanorod second ends 122 of one or more adjacent nanorods 120 may make contact when in close proximity. Moreover, for example, when in close proximity, the nanorod second ends intersect a light path of the illumination source. As such, the nanorods are spaced apart from one another in a set or group by a distance sufficient to allow the nanorod second ends to move in close proximity to one another in the set.

In some examples, the sufficiently flexible polymeric material of the nanorods 120 includes, but is not limited to, polymethyl methacrylate (PMMA), polydimethylsiloxane (PDMS), siloxane, polycarbonate, a photosensitive resist material, a nano-imprint resist material and other thermoplastic polymers and ultra-violet (UV) curable materials comprising one or more of a monomer, an oligomer, a polymer, or a combination of any of these. In other examples, the sufficiently flexible inorganic material of the nanorods 120 includes, but is not limited to, silicon, a silicon oxide, silicon nitride, alumina, diamond, a diamond-like carbon, aluminum, copper, and a combination of any of these inorganic materials. In some examples, the nanorods 120 may comprise a combination of a polymeric material and an inorganic material that has sufficient flexibility as defined above.

In some examples, the sensing substrate 110 is made of a rigid or semi-rigid material including, but not limited to, glass, polymers, silicon, ceramics, metals, and metal oxides. In other examples, the sensing substrate 110 may be made from a relatively flexible material or comprise a flexible material layer to which the nanorods 120 are attached. For example, the flexible material of or on the substrate may be a stimulus responsive material that changes one or more of size, shape and volume (e.g., specific volume) in response to an externally applied stimulus. In particular, as defined herein, the change in size, shape or volume of the stimulus responsive material when exposed to the applied stimulus is sufficient to move the second ends 122 of adjacent nanorods 120 between a spaced apart configuration (inactive) and into close proximity (an active configuration). In the presence of a stimulus responsive material or a flexible substrate, the nanorods 120 may be flexible, rigid or semi-rigid. Examples of stimuli including, but not limited to, one or more of pH, temperature, an electromagnetic field, a sorbate, a concentration of a substance in a sorbate, and various specific chemical triggers. A 'sorbate' is generally any material that may be taken up by the stimulus responsive material using one or more of absorption, adsorption, or a combination of absorption and adsorption, for example. In some examples, the sorbate is one of water, an aqueous solution, and an organic material. In some examples, the stimulus responsive material may comprise a hydrogel or similar super absorbent polymer (SAP). Examples of hydrogels include, but are not limited to, cross-linked polyacrylamides and polyacrylates.

In some examples, the nanorods 120 are movable into and out of close proximity using one or more of a variety of mechanisms including, but not limited to, microcapillary forces, van der Waals interactions, electric charge, electromagnetic force, mechanical force, temperature, and pH, for example. Movement into and out of close proximity is reversible in some examples, while in other examples, the movement may be relatively nonreversible. For example, nanorods may be made of two different materials each having a different thermal expansion rate that causes reversible bending of adjacent nanorods into close proximity to each other with temperature. In another example, microcapillary forces due to evaporation of solvent around the nanorods cause movement of adjacent nanorods into close proximity, for example by bending, whereas re-introduction of a solvent may cause movement of the nanorod second ends out of close proximity.

In some examples, the nanorods 120 comprise a Raman active surface (not illustrated). The Raman active surface may range from a coating of a Raman-active material on the entire nanorod 120 to the coating concentrated at the second ends 122 of the nanorods 120. By definition herein, a Raman-active material is a material that facilitates Raman scattering and the production or emission of a Raman scattering signal during Raman spectroscopy. Raman-active materials include, but are not limited to, gold, silver, platinum, and other noble metals, as well as aluminum and copper and a combination of any of these metals, for example in the form of alloys or layers. For example, the Raman active surface may comprise a multilayer structure of about 10 nm to about 100 nm thick layer of silver having an overcoat layer of about 1 nm to about 50 nm of gold. In some examples, the Raman active surface may comprise a gold layer with a silver overcoat layer. In some examples, the Raman active surface is formed by physical vapor deposition methods, such as e-beam evaporation, thermal evaporation or sputtering. The Raman active materials will not only form on the nanorod tips, but also can land on a side-wall of the nanorods and on the substrate where there are no nanorods anchored or attached.

In some examples, the Raman-active surface comprises a layer or layers having nanoscale surface roughness (e.g., generally coated with metal) that may enhance Raman scattering. Nanoscale surface roughness is generally provided by nanoscale surface features on the surface of the layer(s). Nanoscale surface roughness may be produced spontaneously during deposition of the Raman-active material layer(s) (e.g., gold deposition), for example. In another example, surface roughness may be intentionally induced (e.g., using a laser beam). In some examples, the Raman-active surface comprises a layer of nanoparticles coating the nanorod surface. For example, a monolayer of gold nanoparticles may be used to coat the nanorods 120 and produce the Raman-active surface. The layer of nanoparticles may provide a nanoscale roughness that enhances Raman scattering, for example. In some examples, the Raman-active materials on the nanorods can be an 'ice hockey puck' shape with rounded edges. In accordance with the principles herein, the nanorod second ends 122, especially in close proximity, serve as nanoantennas to concentrate an illumination field to enhance the strength of a Raman scattering signal, for example. The layer of nanoparticles coating the nanorods in this example is integral to or an integral portion of the nanorods 120 relative to the nanoparticle 130, which is described further below.

In some examples, the nanorods 120 further comprise a functionalized surface, in particular on the nanorod second ends 122. In some examples, the functionalized surface comprises a moiety 127 having a selective or specific linking or association capability. The linking or association capability of the moiety 127 is selective to either an analyte or another linking moiety, as described further below. As such, the functionalized surface of the nanorods 120 facilitates an interaction with the analyte or the other linking moiety that is detectable when the nanorod second ends 122 are in close proximity. In some examples, the functionalized surface of the nanorods 120 further comprises a blocking agent 129 configured to block non-specific binding to the nanorods 120 including to the second ends 122, also as further described below.

The SERS sensor 100 further comprises the nanoparticle 130 having a functionalized surface 132 that is independent or non-integral to the nanorods 120. The nanoparticle 130 may be made of a material that includes, but is not limited to, a metal, a semiconductor, a quantum dot, a dielectric, and a combination of these. For example, the nanoparticle 130 may be made of a metal coated polymer particle. The functionalized surface 132 of the nanoparticle 130 comprises a Raman signal generator to generate a Raman scattering signal or 'Raman signal'. In some examples, the Raman signal generator is a Raman dye 135. Examples of Raman dyes useful as the Raman signal generator include, but are not limited to, cyanine dyes, e.g., Cy3 and Cy5, Rhodamine 6G, 4-mercaptobenzene, 4-nitrobenzenethiol, phenyl derivatives, and pyridinyl derivatives.

In some examples, the functionalized surface 132 of the nanoparticle 130 further comprises a moiety 137 having a selective or specific linking or association capability. The linking or association capability of the moiety 137 is selective to either an analyte or the linking moiety 127 on the nanorods 120. As such, the functionalized surface 132 of the nanoparticle 130 facilitates an interaction between the nanoparticle 130 and the nanorods 122 that is detectable when the nanorod second ends 122 are in close proximity to each other. In some examples, the Raman dye 135 may be linked to the selective linking moiety 137 instead of to the nanoparticle surface 132. In this example, the linkage may be a chemical bond, where the linked moiety-Raman dye species provides the nanoparticle 130 with both a Raman signal generator and selective linking capability to an analyte or the linking moiety 127. FIG. 1 illustrates both a linking moiety 137 and a separate Raman dye 135 on the functionalized surface 132 of the nanoparticle 130 by way of example.

In some examples, the functionalized surfaces of the nanoparticle 130 and the nanorods 120 further comprise respective blocking agents 129, 139 configured to independently block non-specific binding to the nanorods 120 and the nanoparticle 130. Examples of blocking agents include, but are not limited to, polyethylene glycol (PEG), polyvinyl alcohol (PVA), polyvinylpyrrolidone (PVP), polyacrylic acid (PAA), polyacrylic maleic acid (PAMA), and a combination of any of these. Other examples of blocking agents include, but are not limited to, bovine serum albumin (BSA), casein, milk, poly-L-Lysine, phosphorothioate oligodeoxynucleotides (PS-ODN), Tween-20, Triton X-100, fish gelatin, or whole sera, and any combination of one or more thereof. In particular, respective blocking agents 129, 139 on the surface of the nanorods 120 and on the surface of the nanoparticle 130 facilitate the interaction between the nanoparticle 130 and the nanorods 120 of the sensor 100 in presence of an analyte that is detectable.

In accordance with the principles herein, the interaction between the nanoparticle 130 and the nanorods 120 involves either association or dissociation. In some examples, the interaction is association. In association for example, the linking moiety 137 on the nanoparticle 130 is configured to selectively associate with a specific analyte. In the presence of the specific analyte, the nanoparticle linking moiety 137 binds or otherwise associates to the specific analyte, for example to a specific binding site of the analyte. For example, the analyte may be selected from a nucleic acid, a protein, a carbohydrate, a lipid, a virus, a viral byproduct, a bacterium, a bacterial byproduct, other toxic organisms and byproducts thereof, a toxin, a toxicant, a drug, a chemical, a portion of any thereof, and a combination of one or more thereof. Exposure of the nanoparticle 130 to an environment that includes the specific analyte results in an association between the analyte and the nanoparticle 130 via the nanoparticle linking moiety 137. As a result, an analyte-nanoparticle complex is formed. Depending on the analyte, the environment may be a fluid, for example a gas environment or a liquid environment. In some examples, a liquid solution comprising the nanoparticle 130 and the analyte may be a buffered solution (i.e., an analyte conjugated solution).

Moreover in association, the linking moiety 127 on the nanorod second ends 122 is configured to be selective to the same analyte described above, albeit the selectivity is to a different, separate binding site on the same analyte or a different, separate binding mechanism to the same analyte. When exposed to the analyte-nanoparticle complex in solution, for example, the linking moiety 127 on the nanorod second ends 122 binds or otherwise associates to the same analyte in a location on the analyte that is different from where the nanoparticle 130 is bound. The interaction between the nanorods 120 of the sensing substrate 110 and the analyte-nanoparticle complex is detectable when the nanorod second ends 122 are in the close proximity to each other. For example, the Raman dye 135 on the interacted nanoparticle 130 is configured to generate a Raman scattering signal that the nanorod second ends 122 in close proximity enhances. Therefore, the analyte itself need not produce a Raman scattering signal for detection according to the principles described herein.

In an example, the analyte is or comprises prostate specific antigen (PSA). The linking moiety 127 on the nanorods 120 and the linking moiety 137 on the nanoparticle 130 may be anti-mouse PSA and anti-goat PSA, respectively, or vice versa. In another example, the analyte is or comprises streptavidin or avidin. In this example, the linking moieties 137 and 127 may be each biotin that separately associates with the analyte.

In dissociation, the linking moiety 137 on the nanoparticle 130 is configured to selectively associate with the linking moiety 127 on the second ends 122 of the nanorods 120 of the sensing substrate 110. The nanoparticle linking moiety 137 binds or otherwise associates to the nanorod linking moiety 127. The nanorod second ends 122 are in close proximity, and a Raman scattering signal generated by the Raman dye 135 on the nanoparticle 130 is detectable on the nanorod-nanoparticle complexes. Further in dissociation, the sensing substrate 110 of nanorod-nanoparticle complexes is exposed to a specific analyte to be detected. The specific analyte selectively attacks (e.g., lyses or cleaves) one or more of the nanoparticle linking moiety 137, the nanorod linking moiety 127 and the linkage type (e.g., bond) of the linking moieties 127, 137 to selectively break apart or dissociate the association between the nanoparticle 130 and the nanorods 120 on the sensing substrate 110. In other words, one of the linking moiety 137, the linking moiety 127 and the type of linkage between the moieties 127, 137 is configured to be a specific target of a specific analyte. The interaction between the nanoparticle 130 and the nanorods 120 is changed (i.e., dissociated) by the presence of the specific analyte which is detectable by an effect that the dissociation has on the generated Raman scattering signal by the nanoparticle Raman dye 135. The effect is that the Raman scattering signal decreases in proportion to the number of nanoparticles 130 that are dissociated by the analyte from the nanorod second ends 122 in close proximity to each other.

In accordance with the principles herein, the respective linking moieties 127, 137 on the nanorods 120 and the nanoparticles 130 are configured to selectively or specifically bind, associate or otherwise interact with either a particular analyte or the other of the linking moieties 137, 127. The respective interactions may be independently one or more of covalent bonding, ionic bonding, non-covalent bonding, hydrogen bonding, and dipole-dipole interactions, for example.

For example, the nanoparticle 130 may be populated with a linking moiety 137 that is member of a specific binding pair. Examples of specific binding pairs include, but are not limited to, a receptor-ligand, an antibody-antigen, enzyme-active site key, DNA-RNA, DNA-protein, RNA-protein, complementary nucleic acid pairs, and a combination of one or more of these. For example, a receptor of a specific receptor-ligand binding pair may be functionalized on the nanoparticle surface 132 as the linking moiety 137 (alternatively, the ligand of the specific receptor-ligand binding pair may be used). The example receptor linking moiety 137 is configured to bind with the specific ligand, i.e., the other member of the specific binding pair. In some examples, the specific ligand may be an analyte to be detected, or a portion or a byproduct of the analyte to be detected (i.e., a target species). The linking moiety 127 on the nanorod second ends 122 also specifically and separately binds with the specific ligand analyte species to be detected with the SERS sensor 100 by association.

In others of these examples, the specific ligand, or relevant portion thereof, of the specific binding pair may be the linking moiety 127 on the nanorod second ends 122. The receptor moiety 137 on the nanoparticle 130 and the specific ligand moiety 127 on the nanorod second ends 122 are associated on the SERS sensing substrate 110. In these examples, the analyte or target species to be detected specifically and characteristically lyses or severs some aspect of the linkage between the receptor moiety 137 on the nanoparticle 130 and the specific ligand moiety 127 on the nanorods 120 that is detected with the SERS sensor 100 by dissociation, as described above.

Analyte species that may cleave some aspect of the linkage between the linking moieties 127, 137 include, but are not limited to, one or more of a lipase (for lipid-containing linking moieties), amylase (for amylase-, starch- and maltodextrin-containing linking moieties), proteases (for protein-containing linking moieties), and nucleases (for nucleic acid-containing linking moieties), for example.

Figure 2A:
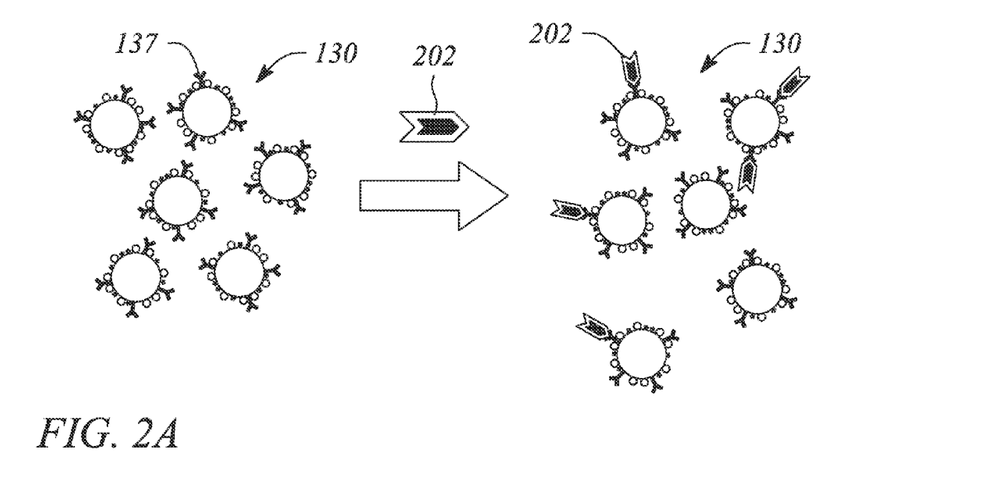
FIGS. 2A-2C illustrate schematic views of surface enhanced Raman spectroscopy (SERS) sensing by way of association with an analyte according to an example in accordance with the principles described herein.
Figure 2B:
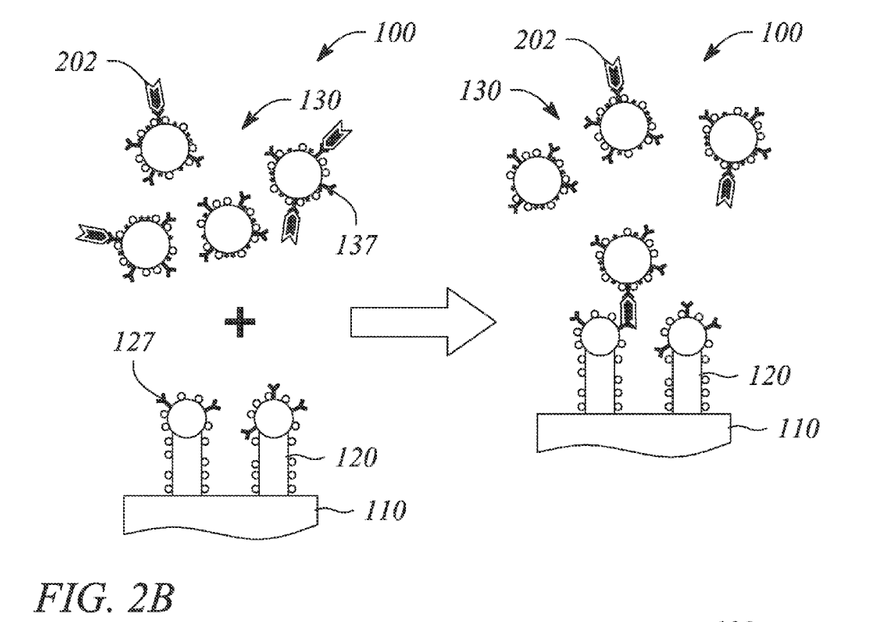
Figure 2C:
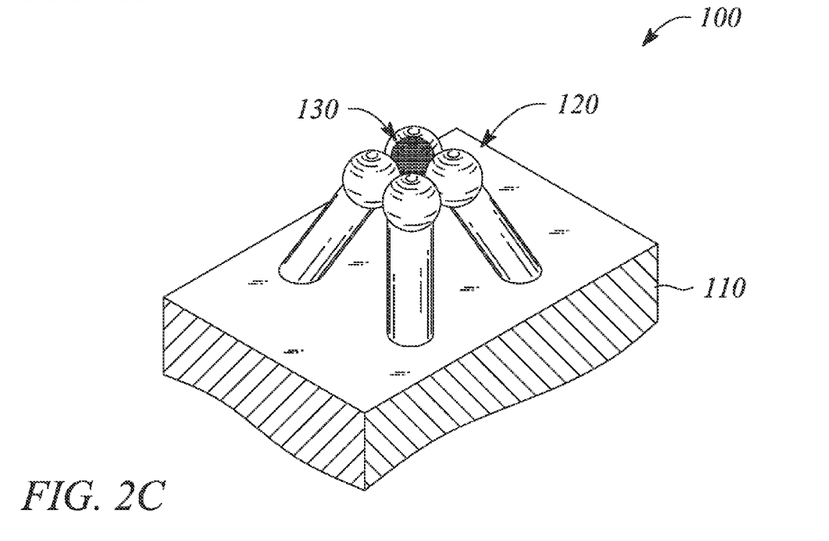

FIGS. 2A-2C illustrate the association mechanism for sensing an analyte in an example in accordance with the principles described herein. In the schematic side view in FIG. 2A, a Raman reporter solution comprising a plurality of the above-described functionalized nanoparticle 130 is exposed to an analyte 202. Some of the nanoparticle linking moieties 137 that are specific to the analyte 202 bind or associate with the analyte 202 to form an analyte-conjugated solution of analyte-nanoparticle complexes. In the schematic side view in FIG. 2B, the sensing substrate 110 of nanorods 120 is exposed to the analyte-conjugated solution. Some of the nanorod linking moieties 127 that are specific to a separate binding site of the analyte 202 in the analyte-nanoparticle complexes bind or associate with the analyte-nanoparticle complexes at the nanorod second ends to form nanorod-analyte-nanoparticle complexes. FIG. 2C illustrates a schematic perspective view of the result of evaporating a solvent in the analyte-conjugated solution. The second ends of the nanorods 120 of the sensor 100 are brought into close proximity by the solvent evaporation for detection of the Raman signal from the functionalized nanoparticles 130 of the analyte-nanoparticle complexes captured by the nanorods 120 and concentrated at the nanorod second ends.

Figure 3A:
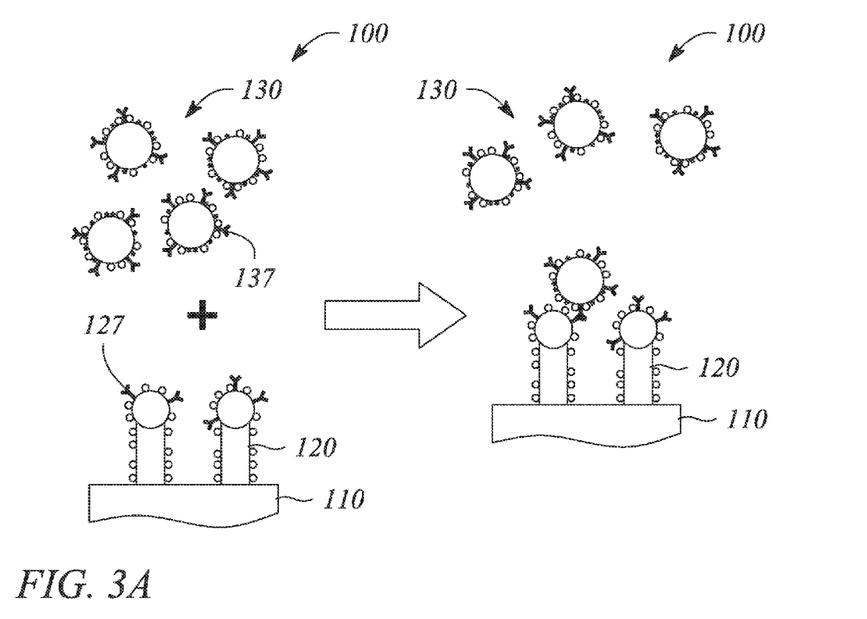
FIGS. 3A-3C illustrate schematic views of surface enhanced Raman spectroscopy (SERS) sensing by way of dissociation by an analyte according to another example in accordance with the principles described herein.
Figure 3B:
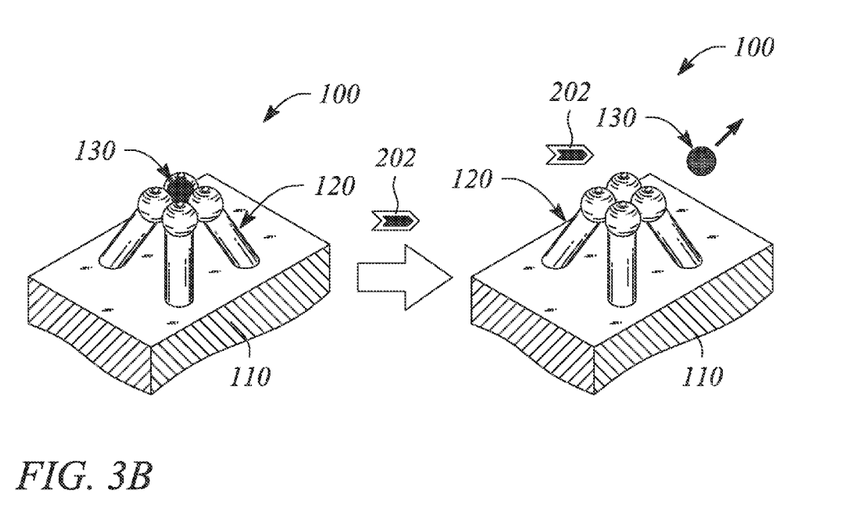
Figure 3C:
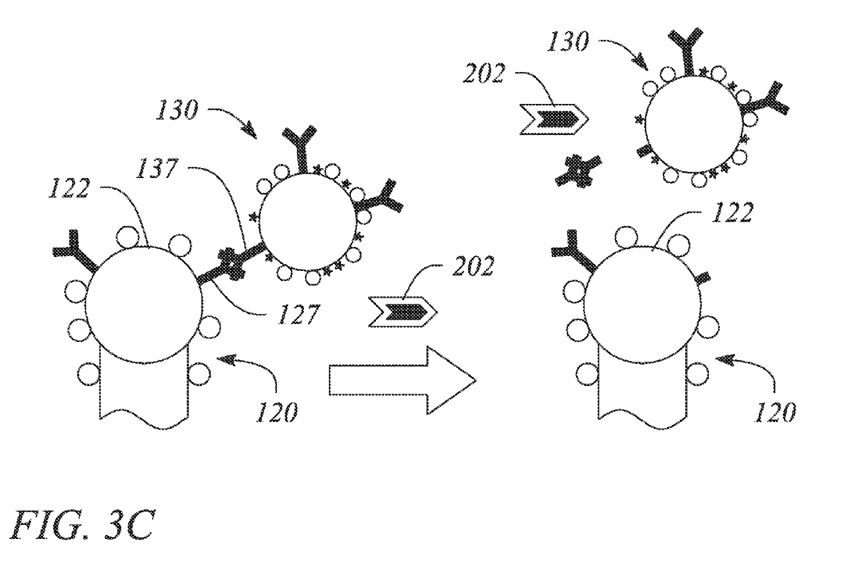

FIGS. 3A-3C illustrate the dissociation mechanism for sensing an analyte in an example in accordance with the principles described herein. In the schematic side view of FIG. 3A, a Raman reporter solution comprising a plurality of the above-described functionalized nanoparticle 130 is exposed to the above-described sensing substrate 110 comprising the nanorods 120. The nanorod linking moieties 127 and the nanoparticle linking moieties 137 are specific to each other, for example they may be members of a specific binding pair. The nanoparticles 130 in the Raman reporter solution bind or associate with the nanorods 120. In the schematic perspective view of FIG. 3B, solvent from the Raman reporter solution is evaporated to bring the nanorod second ends into close proximity with the nanoparticle 130 concentrated at the nanorod second ends of the sensor 100. The sensor 100 is exposed to an analyte 202 that specifically attacks either the linkage between the linking moieties 127, 137 or one of the linking moieties 127, 137 to ultimately dissociate the nanoparticle 130 from the nanorods 120 of the sensing substrate 110, which is detectable as a decrease in the Raman signal from the Raman dye on the nanoparticle 130 as it is released from the nanorod second ends in close proximity. FIG. 3C illustrates a magnified schematic side view of an example of the dissociation of the nanoparticle 130 from the nanorod second end 122 by way of the specific analyte 202 severing the linkage between linking moieties 127, 137 into one or more pieces.

Figure 4:
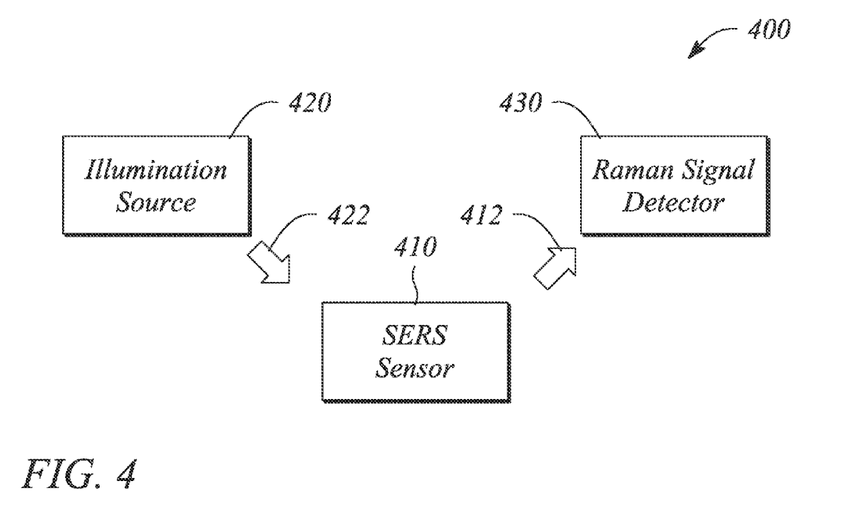
FIG. 4 illustrates a block diagram of a surface enhanced Raman spectroscopy (SERS) sensor system according to an example in accordance with the principles described herein.

FIG. 4 illustrates a block diagram of a SERS sensor system 400 according to an example of the principles described herein. The SERS sensor system 400 detects an analyte using a Raman scattering signal 412 from a functionalized surface of a nanoparticle based on an interaction of the nanoparticle with nanorods on a sensing substrate. The system 400 comprises a SERS sensor 410 that is substantially the same as described above for the SERS sensor 100. The system 400 further comprises an illumination source 420 and a Raman signal detector 430.

The illumination source 420 is directed at the sensing substrate of the SERS sensor 410, and in particular, the illumination source 420 is configured to illuminate second ends or tips of adjacent nanorods on the sensing substrate in a close proximal relationship to each other, which is also described above for the SERS sensor 100. The illumination source 420 may emit an illumination signal 422 comprising a beam of electromagnetic (EM) radiation (e.g., an optical beam or optical signal) having a frequency that stimulates emission of the Raman scattering signal 412 by the functionalized nanoparticle surface. In some examples, the illumination source 420 may comprise a laser and the illumination signal 422 may comprise a laser beam. In other examples, the illumination source 420 may be other means for generating the EM radiation (e.g., a light emitting diode or an incandescent light source). In some examples, the nanorod second ends do not intersect the illumination beam from the illumination source 420 unless or until the nanorod second ends are in close proximity to each other.

The Raman signal detector 430 is arranged to detect the Raman signal from a vicinity of the nanorod second ends in close proximity to each other. In particular, the Raman signal detector 430 is configured to receive the Raman scattering signal 412 generated from the functionalized surface of the nanoparticles associated with the nanorod second ends in close proximity on the sensing substrate of the SERS sensor 410. In some examples, the Raman signal detector 430 is configured to detect a change (e.g., decrease) in the Raman scattering signal 412 if the nanoparticles are dissociated from the nanorods of the sensing substrate in the presence of an analyte.

In some examples not illustrated, the SERS sensor system 400 further comprises sets of the functionalized nanoparticles. Each nanoparticle set is functionalized with a Raman dye and a corresponding first linking moiety on a surface of the nanoparticles of the respective set that are different from other nanoparticle sets. The Raman dye in a set differs from other sets by having a Raman signal that is different from the Raman signals from other sets, for example, to distinguish the sets. The first linking moiety in each set differs by being association specific either to different analytes or to different nanorods of the sensing substrate, in some examples. In other examples, the first linking moieties in each set differ by being dissociation specific to different analytes. The Raman dye and the corresponding first linking moiety in a set are specific to a particular analyte. The specificity correlates a respective Raman scattering signal to the particular analyte.

In some examples (also not illustrated), the SERS sensor system 400 further comprises sets of nanorods on the sensing substrate. Each nanorod set comprises a second linking moiety on the nanorods that is different from other nanorod sets. The second linking moieties differ by being association-specific to either the different analytes or the different first linking moieties of the nanoparticle sets. In other examples, the second linking moieties in each set differ by being dissociation specific to different analytes. The specificity provided by the SERS sensor system 400 according to these examples facilitates multiplexing detection of a variety of different analytes with a single SERS sensor 410.

Figure 5:
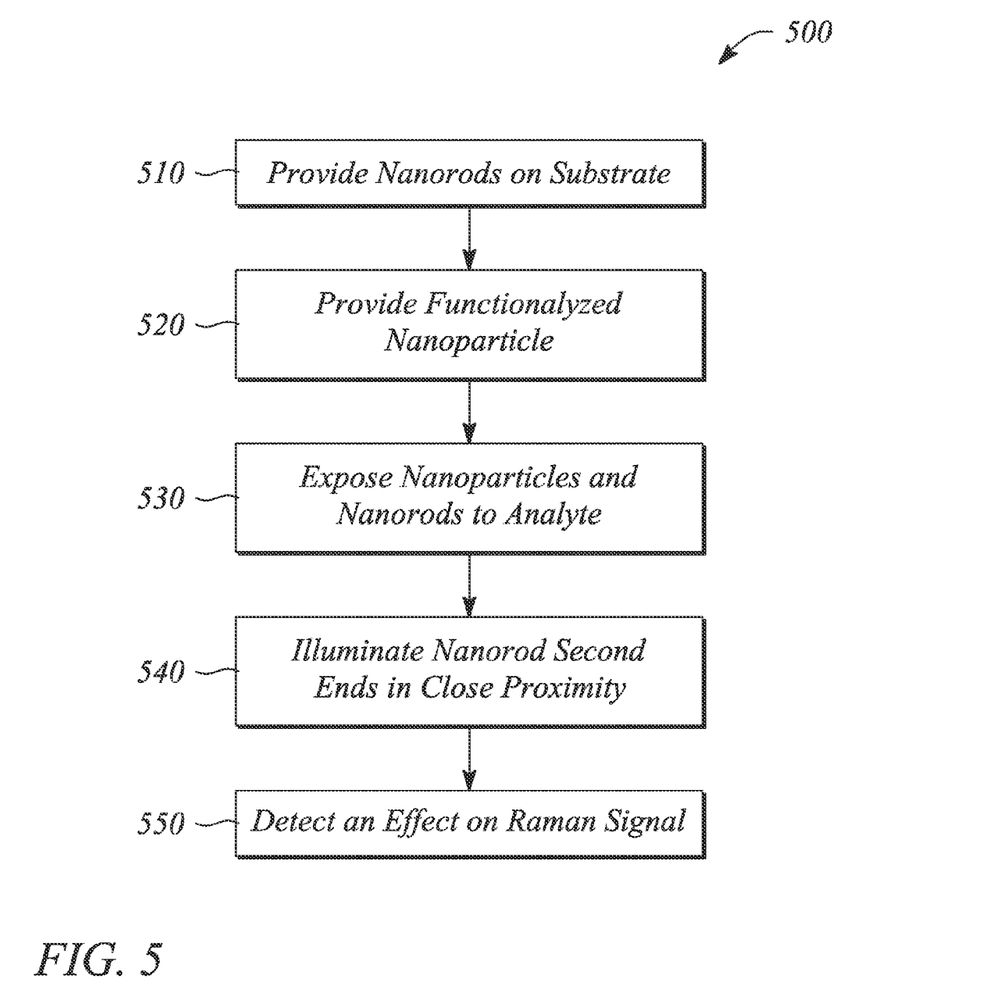
FIG. 5 illustrates a flow chart of a method of surface enhanced Raman spectroscopy (SERS) sensing according to an example in accordance with the principles described herein.

FIG. 5 illustrates a flow chart of a method 500 of SERS sensing according to an example of the principles described herein. The method 500 of SERS sensing comprises providing 510 a plurality of nanorods spaced apart and attached at first ends to a substrate. Each nanorod of the plurality has a free, second end opposite the first end of the nanorod. In some examples, the nanorods are relatively flexible to bend such that the second ends of adjacent nanorods are movable into close proximity to each other. In some examples, the substrate is or comprises a flexible material or a stimulus responsive material that facilitates movement of the second ends of adjacent nanorods into close proximity to each other. The nanorods comprise a Raman active surface either concentrated at the second ends or as a coating on along all or a portion of the nanorod length that includes the second ends, for example. Moreover, the surface of the nanorod second ends is functionalized with a linking moiety. In some examples, the nanorods provided 510 on the substrate are substantially the same as the nanorods 120 on the sensing substrate 110 of the SERS sensor 100 described above.

The method 500 of SERS sensing further comprises providing 520 a plurality of nanoparticles that are functionalized. The nanoparticles are functionalized on their surface to directly or indirectly interact with the nanorods but are otherwise independent of the nanorods. In some examples, the nanoparticles are functionalized with a Raman signal generator, for example a Raman dye, and a linking moiety that is specific to either an analyte or the linking moiety functionalized on the nanorod second ends. In some examples, the provided 520 functionalized nanoparticles are substantially the same as the functionalized nanoparticles 130 of the SERS sensor 100 described above. Moreover, the provided 510, 520 nanorods on a substrate and the nanoparticles, respectively, form a SERS sensor that is substantially the same as the SERS sensor 100, described above.

Figure 6A:
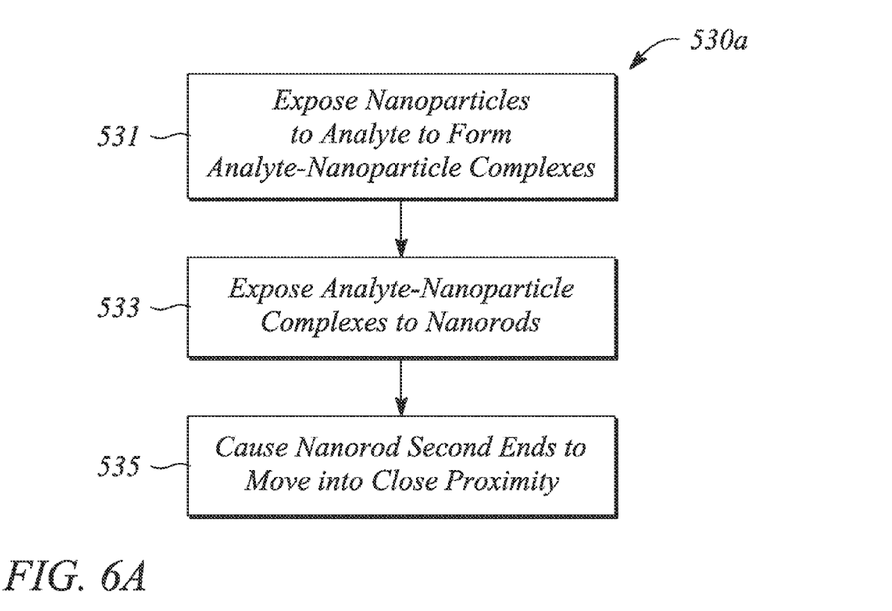
FIG. 6A illustrates a flow chart of exposing the SERS sensor to an analyte in an association mechanism of the method of FIG. 5 according to an example in accordance with the principles described herein.

The method 500 of SERS sensing further comprises exposing 530 the nanoparticles and the nanorods of the SERS sensor to an analyte. FIG. 6A illustrates a flow chart of exposing 530a the SERS sensor to the analyte in the association mechanism of the method 500 of SERS sensing according to an example in accordance with the principles described herein. In association, exposing 530a the SERS sensor comprises exposing 531 the independent nanoparticles to the analyte to form analyte-nanoparticle complexes in solution; and exposing 533 the analyte-nanoparticle complexes in solution to the nanorods to form nanorod-analyte-nanoparticle complexes in solution. Exposing 530a further comprises causing 535 the nanorod second ends to move into close proximity. For example, the solvent from the solution may be evaporated to cause 535 the close proximal relationship between second ends of adjacent nanorods. In other examples, one or more of temperature, pH and other physical or chemical parameters may be altered to cause 535 the close proximity of the second ends.

Figure 6B:
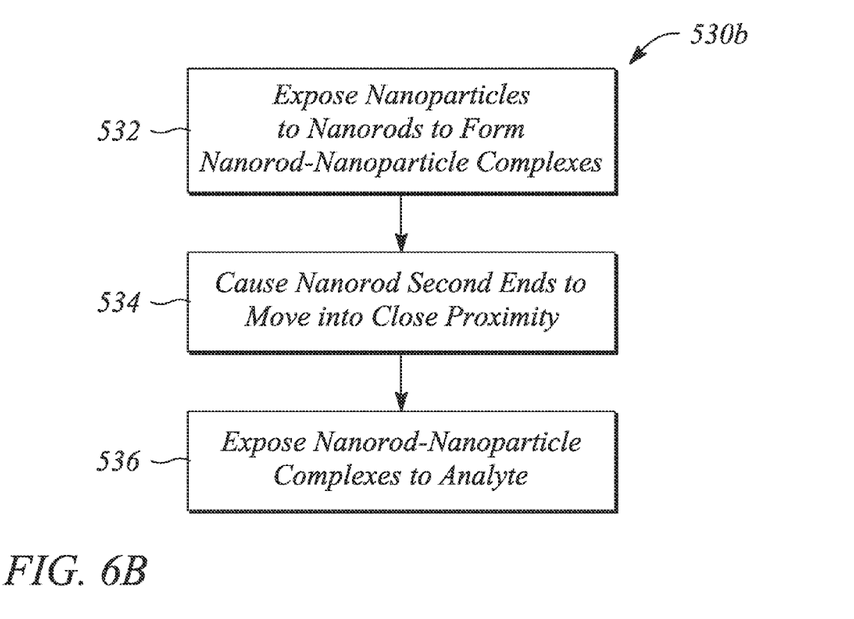
FIG. 6B illustrates a flow chart of exposing the SERS sensor to an analyte in a dissociation mechanism of the method of FIG. 5 according to another example in accordance with the principles described herein.

FIG. 6B illustrates a flow chart of exposing 530b the SERS sensor to the analyte in the dissociation mechanism of the method 500 of SERS sensing according to another example in accordance with the principles described herein. In dissociation, exposing 530b the SERS sensor comprises exposing 532 the independent nanoparticles to the nanorods to form nanorod-nanoparticle complexes; causing 534 the nanorod second ends to move into close proximity; and exposing 536 the nanorod-nanoparticle complexes with the second ends in close proximity to the analyte. For example, one or more of solvent evaporation, temperature change, pH change and other physical or chemical changes may be used to cause 534 the close proximal relationship between second ends of adjacent nanorods.

Referring back to FIG. 5, the method 500 of SERS sensing further comprises illuminating 540 the nanorod second ends in close proximity which effectively illuminates an interaction between the nanoparticles and the nanorod second ends to generate a Raman signal. In association, the illuminated 540 interaction comprises the independent nanoparticles and the nanorod second ends both selectively associated to the analyte in nanorod-analyte-nanoparticle complexes (i.e., an indirect interaction between the nanoparticles and the nanorods). In dissociation, the illuminated 540 interaction comprises the independent nanoparticles and the nanorod second ends in close proximity selectively associated to each other in nanorod-nanoparticle complexes (i.e., a direct interaction between the nanoparticles and the nanorods) and the analyte selectively dissociating the nanoparticles from the nanorods.

The method 500 of SERS sensing further comprises detecting 550 an effect on the Raman scattering signal from the functionalized nanoparticles caused by the analyte. In association, the effect on the Raman scattering signal is generation of the Raman scattering signal as a result of the interaction between the nanoparticles and the nanorods with the analyte (i.e., indirect interaction). In dissociation, the effect on the Raman scattering signal is a decrease in a Raman scattering signal generated as a result of the interaction between the nanoparticles and the nanorods (i.e., direct interaction). The decrease in the generated Raman scattering signal is due to the dissociation of the direct interaction in the presence of the analyte.

Thus, there have been described examples of a SERS sensor, a SERS sensor system and a method of SERS sensing using a sensing substrate populated with nanorods and functionalized nanoparticles that are independent of the nanorods. It should be understood that the above-described examples are merely illustrative of some of the many specific examples that represent the principles described herein. Clearly, those skilled in the art can readily devise numerous other arrangements without departing from the scope as defined by the following claims.

What is claimed is:
1. A surface enhanced Raman spectroscopy (SERS) sensor comprising:
a sensing substrate comprising at least two spaced apart nanorods attached at first ends to the sensing substrate, the nanorods comprising a Raman active surface; and
a Raman reporter solution exposed to the sensing substrate, the Raman reporter solution including a solvent and a nanoparticle having a functionalized surface comprising a Raman signal generator, the nanoparticle being independent of the nanorods, wherein second ends of the nanorods are movable into close proximity of one another in response to microcapillary forces due to evaporation of the solvent, wherein an interaction between the nanorod second ends in close proximity of one another and the nanoparticle is detectable, and wherein the nanorods and the functionalized surface of the nanoparticle each further comprises a linking moiety and a blocking agent to block non-specific binding to the nanoparticle and the nanorods, wherein the linking moiety of the nanoparticle is bound to the linking moiety of the at least one of the nanorods, and wherein the SERS sensor further comprises, an analyte to attack a linkage between the linking moieties or one of the linking moieties to selectively dissociate the nanoparticle from the nanorods, the dissociation being betectable as a decrease in a Raman signal generated by the interaction.

2. The SERS sensor of claim 1, wherein the Raman signal generator comprises a Raman dye, and a presence of an analyte has an effect on the interaction and on a Raman scattering signal from the Raman dye that is detectable.

3. The SERS sensor of claim 2, wherein the analyte is selected from a nucleic acid, a protein, a carbohydrate, a lipid, a virus, a viral byproduct, a bacterium, a bacterial byproduct, other toxic organisms and byproducts thereof, a toxin, a toxicant, a drug, a chemical, a portion of any thereof, and a combination of one or more thereof.

4. The SERS sensor of claim 1, wherein the functionalized surface of the nanoparticle linking moiety, is a first linking moiety, the nanorods linking moiety is a second linking moiety on the nanorod second ends, the first linking moiety and the second linking moiety facilitating the interaction between the nanoparticle and the nanorod second ends.

5. The SERS sensor of claim 4, wherein the interaction comprises either a direct interaction between the nanoparticle and the nanorod second ends or an indirect interaction between the nanoparticle and the nanorod second ends, a presence of an analyte configured to either facilitate the indirect interaction or dissociate the direct interaction.

6. The SERS sensor of claim 1, wherein the nanorods and the functionalized surface of the nanoparticle each further comprises a linking moiety and a blocking agent to block non-specific binding to the nanoparticle and the nanorods, the interaction comprising the linking moiety on the nanoparticle to selectively bind to an analyte to form an analyte-nanoparticle complex and the linking moiety on the nanorod second ends to selectively bind to the analyte of the analyte-nanoparticle complex to generate a detectable Raman signal.

7. A surface enhanced Raman spectroscopy (SERS) sensor system comprising:

a SERS sensor that includes a sensing substrate comprising spaced apart nanorods attached at first ends to the sensing substrate, the nanorods comprising a Raman active surface; and a Raman reporter solution exposed to the sensing substrate, the Raman reporter solution including a solvent and functionalized nanoparticles independent of the nanorods to interact with nanorod second ends to generate a Raman signal that is detectable when the nanorod second ends are in close proximity to each other, wherein the nanorod second ends are movable into close proximity to each other in response to microcapillary forces due to evaporation of the solvent;

an illumination source directed at the SERS sensor to excite the Raman signal; and a Raman signal detector arranged to detect the Raman signal;

wherein the functionalized nanoparticles comprise a Raman dye and a first linking moiety on the surface of the nanparticles, the nanorods further comprising a second linking moiety on the nanorod second ends, the first linking moiety and the second linking moiety facilitating an interaction between the nanoparticles and the nanorods that generates the Raman signal from the Raman dye; and wherein the first linking moiety and the second linking moiety are specifically complementary to each other to associate the functionalized nanoparticles to the nanorod second ends in a light path of the illumination source, and wherein the SERS sensor system further comprises and analyte to attack a linkage between the first and second linking moieties or one of the first or second linking moieties to selectively dissociate the functionalized nanoparticles from the nanorods, a dissociation of the functionalized nanoparticles from the nanorods to decrease the Raman signal that is detectable by the Raman signal detector.

8. The SERS sensor system of claim 7, wherein the first linking moiety and the second linking moiety are specifically complementary to different interaction sites of an analyte to associate the analyte to both the functionalized nanoparticles and to the nanorod second ends, and wherein association of the linking moieties to the analyte in a light path of the illumination source generates the Raman signal that is detectable by the Raman signal detector.

9. The SERS sensor system of claim 7, further comprising sets of the functionalized nanoparticles, each nanoparticle set being functionalized with a Raman dye and a corresponding first linking moiety on a surface of the nanoparticles that are different from other nanoparticle sets, the different Raman dyes having different Raman signals, the different corresponding first linking moieties being association specific to either different analytes or the nanorods to correlate a respective Raman signal to a particular analyte.

10. The SERS sensor system of claim 9, further comprising sets of the nanorods on the sensing substrate, each nanorod set comprising a second linking moiety on the nanorods that is different from other nanorod sets, the different second linking moieties being association specific to either the different analytes or the different corresponding first linking moieties to multiplex detection of the different analytes.

11. A method of surface enhanced Raman spectroscopy (SERS) sensing, comprising:

providing spaced apart nanorods attached at first ends to a substrate, the nanorods comprising a Raman active surface;

exposing the spaced apart nanorods to a Raman reporter solution including a solvent and functionalized nanoparticles, whereby at least some of the functionalized nanoparticles bind to second ends of at least some of the nanorods;

evaporating the solvent of the Raman reporter solution, thereby bringing the second ends into close proximity with one another;

illuminating the nanoparticles and the nanorods when the second ends are close proximity with one another to generate a Raman signal;

exposing the nanoparticles and the nanorods to an analyte when the second ends into close proximity with one another, thereby dissociating the nanoparticles from the nanorods; and detecting a decrease in the Raman signal.

* * * * *

UNITED STATES PATENT AND TRADEMARK OFFICE
CERTIFICATE OF CORRECTION

PATENT NO. : 9,588,048 B2  
APPLICATION NO. : 14/118801  
DATED : March 7, 2017  
INVENTOR(S) : Ansoon Kim et al.

Page 1 of 1

It is certified that error appears in the above-identified patent and that said Letters Patent is hereby corrected as shown below:

In the Specification

In Column 2, Line 43, delete "nanoparticle facilitates" and insert -- nanoparticle that is functionalized on its surface. The functionalized surface of the nanoparticle facilitates --, therefor.

In the Claims

In Column 12, Lines 60-61, in Claim 1, delete "sensor comprising:" and insert -- sensor, comprising --, therefor.

In Column 13, Line 20 approx., in Claim 1, delete "betectable" and insert -- detectable --, therefor.

In Column 13, Line 33 approx., in Claim 4, delete "moiety, is" and insert -- moiety is --, therefor.

In Column 14, Line 7, in Claim 7, delete "nanparticles," and insert -- nanoparticles, --, therefor.

In Column 14, Line 19 approx., in Claim 7, delete "and analyte" and insert -- an analyte --, therefor.

Signed and Sealed this  
Nineteenth Day of September, 2017

Joseph Matal  
*Performing the Functions and Duties of the*  
*Under Secretary of Commerce for Intellectual Property and*  
*Director of the United States Patent and Trademark Office*